(12) United States Patent  (10) Patent No.: US 9,382,403 B2
Bradshaw  (45) Date of Patent: Jul. 5, 2016

(54) PHENOL-FREE OVERBASED ALKALINE EARTH METAL CARBOXYLATE

(71) Applicant: Ferro Corporation, Mayfield Heights, OH (US)

(72) Inventor: John D. Bradshaw, Solon, OH (US)

(73) Assignee: Polymer Additives, Inc., Independence, OH (US)

( * ) Notice: Subject to any disclaimer, the term of this patent is extended or adjusted under 35 U.S.C. 154(b) by 0 days.

(21) Appl. No.: 14/332,510

(22) Filed: Jul. 16, 2014

(65) Prior Publication Data

US 2016/0017118 A1   Jan. 21, 2016

(51) Int. Cl.
C08K 5/098 (2006.01)
C07C 51/41 (2006.01)
C07D 307/44 (2006.01)
C09D 7/00 (2006.01)
C08K 5/1535 (2006.01)
C08K 13/02 (2006.01)
C08L 57/08 (2006.01)

(52) U.S. Cl.
CPC ............... *C08K 5/098* (2013.01); *C07C 51/414* (2013.01); *C07D 307/44* (2013.01); *C08K 5/1535* (2013.01); *C08K 13/02* (2013.01); *C08L 57/08* (2013.01); *C09D 7/00* (2013.01)

(58) Field of Classification Search
CPC .................... C08K 5/098; C07C 51/41
See application file for complete search history.

(56) References Cited

U.S. PATENT DOCUMENTS

| 6,811,722 | B2 * | 11/2004 | Zhou | C08K 5/103 252/182.13 |
| 7,498,372 | B2 * | 3/2009 | Schaefer | C08K 5/10 524/308 |
| 2009/0312470 | A1 * | 12/2009 | Bradshaw | C07C 67/08 524/285 |

* cited by examiner

*Primary Examiner* — Robert Harlan
(74) *Attorney, Agent, or Firm* — Black, McCuskey, Souers & Arbaugh, LPA

(57) ABSTRACT

A phenol-free overbased alkaline earth metal carboxylate is obtained by reacting a cyclic ether alcohol, an alkaline earth metal hydroxide, a fatty carboxylic acid, carbon dioxide, an optional fatty alcohol, and an optional liquid hydrocarbon solvent or oil.

3 Claims, 4 Drawing Sheets

Traditional Reaction Scheme including Alkylphenol for producing Overbased Barium Carboxylate.

Figure 1. Traditional Reaction Scheme including Alkylphenol for producing Overbased Barium Carboxylate.
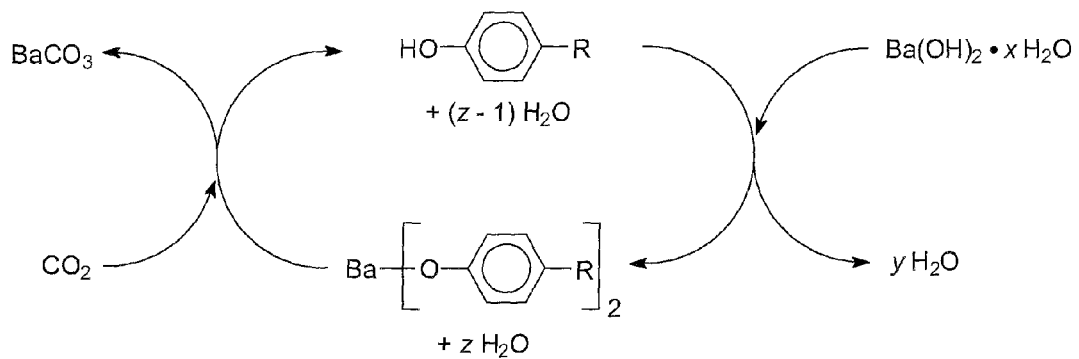
Figure 2. Inventive reaction scheme with cyclic ether hydroxide intermediate to make Overbased Barium Carboxylate.
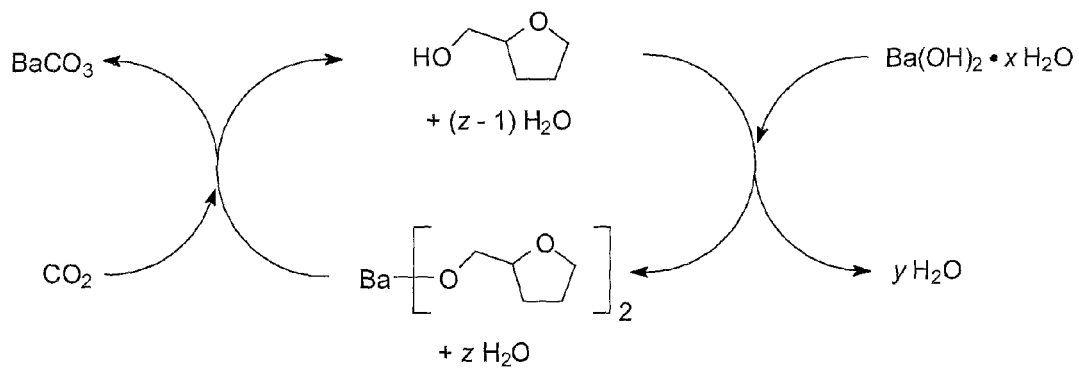

Figure 3. Heat Stability Test of Compounds I – IV at 190 °C
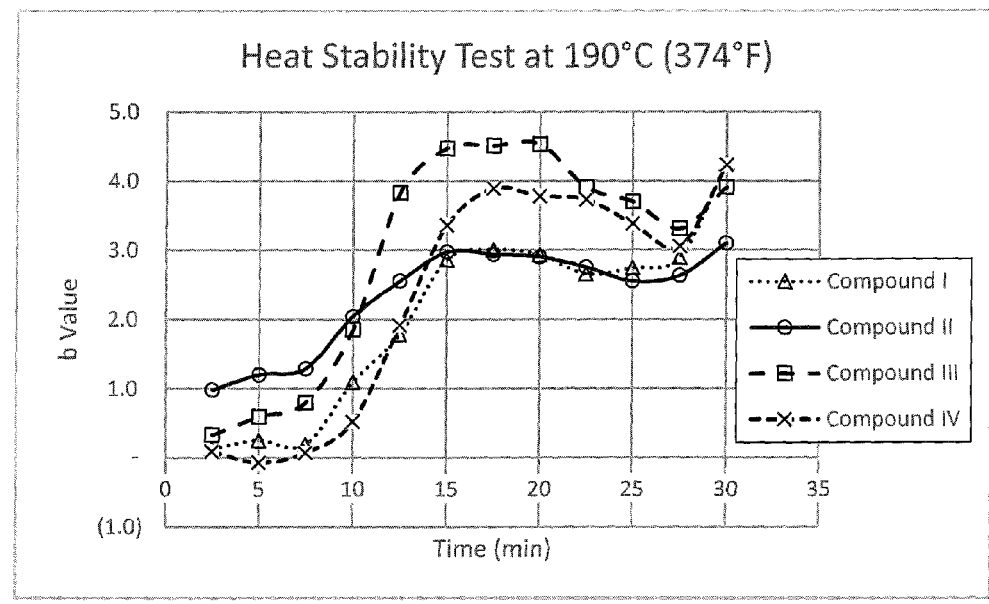
Figure 4. Heat Stability Test of Compounds V-VII at 190 °C
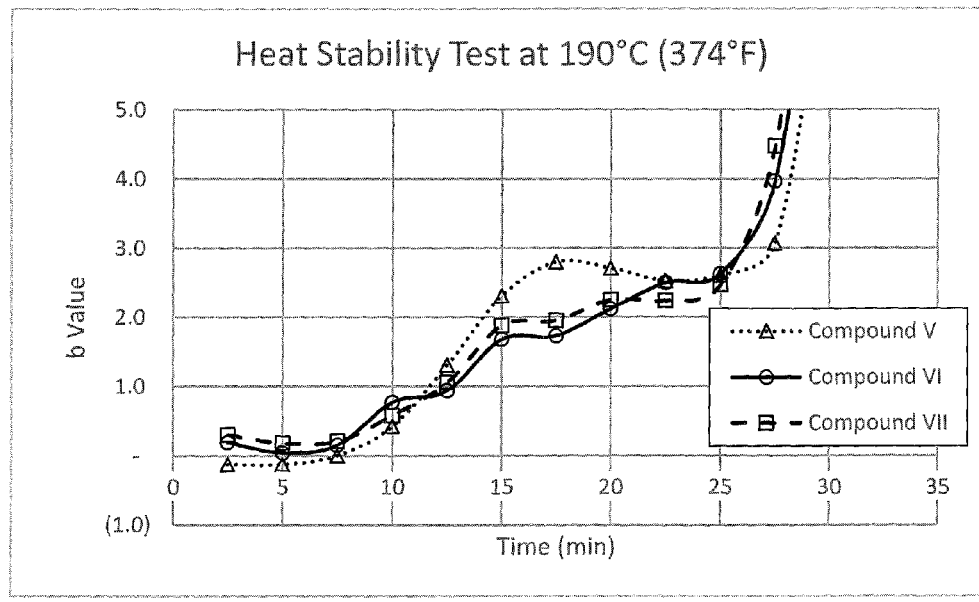

Figure 5. Heat Stability Test of Compounds VIII-X at 190 °C
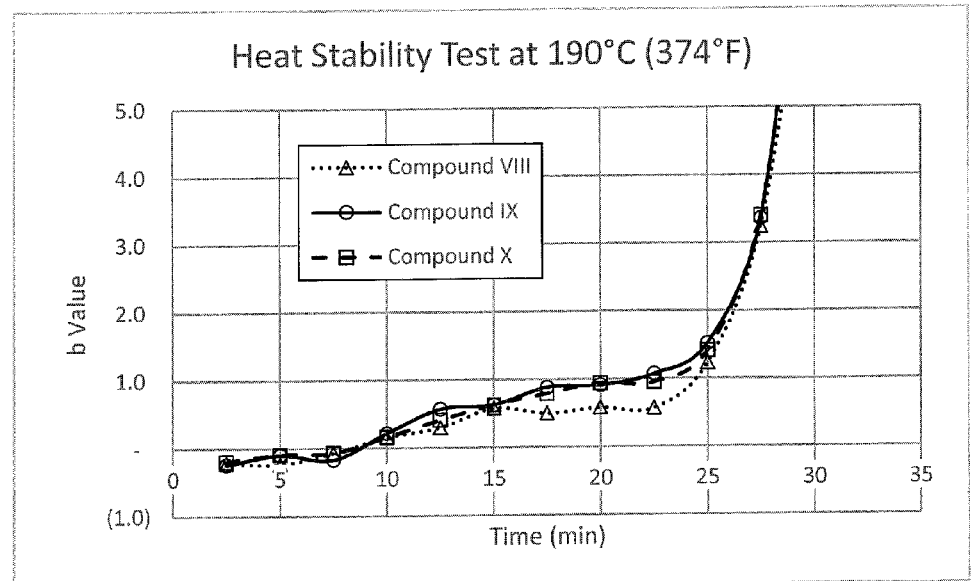
Figure 6. Heat Stability Test of Compounds I-IV at 200 °C
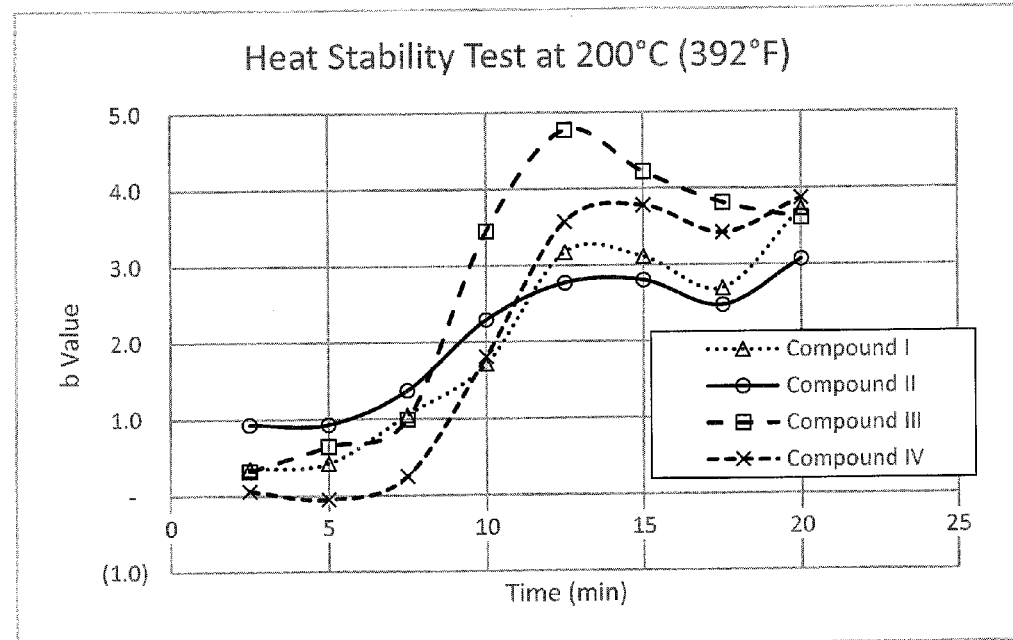

Figure 7. Heat Stability Test of Compounds V-VII at 200 °C
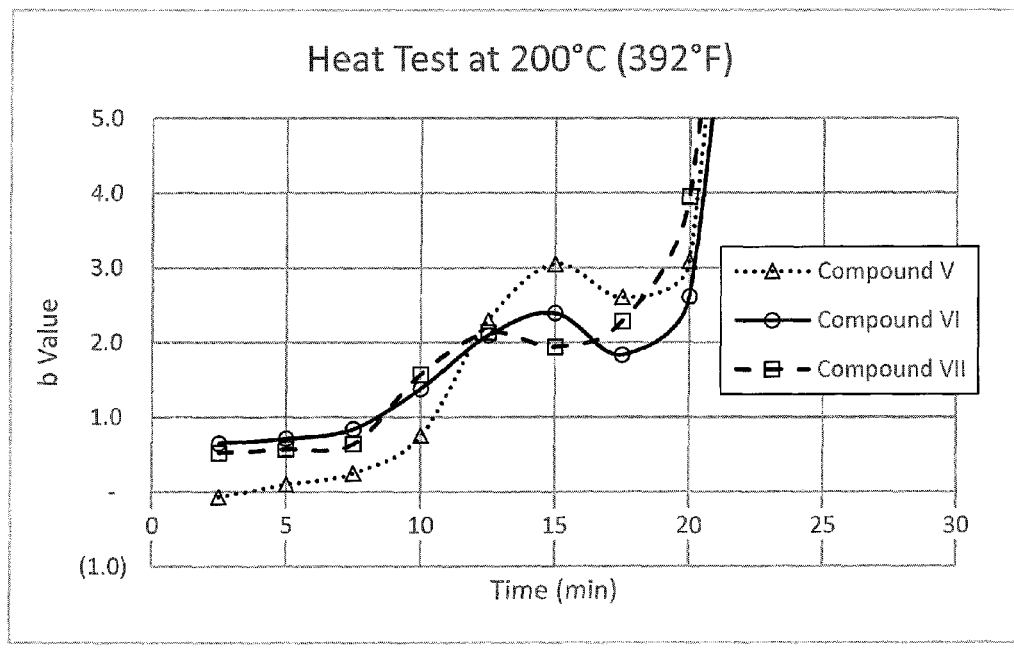
Figure 8. Heat Stability Test of Compounds VIII-X at 200 °C
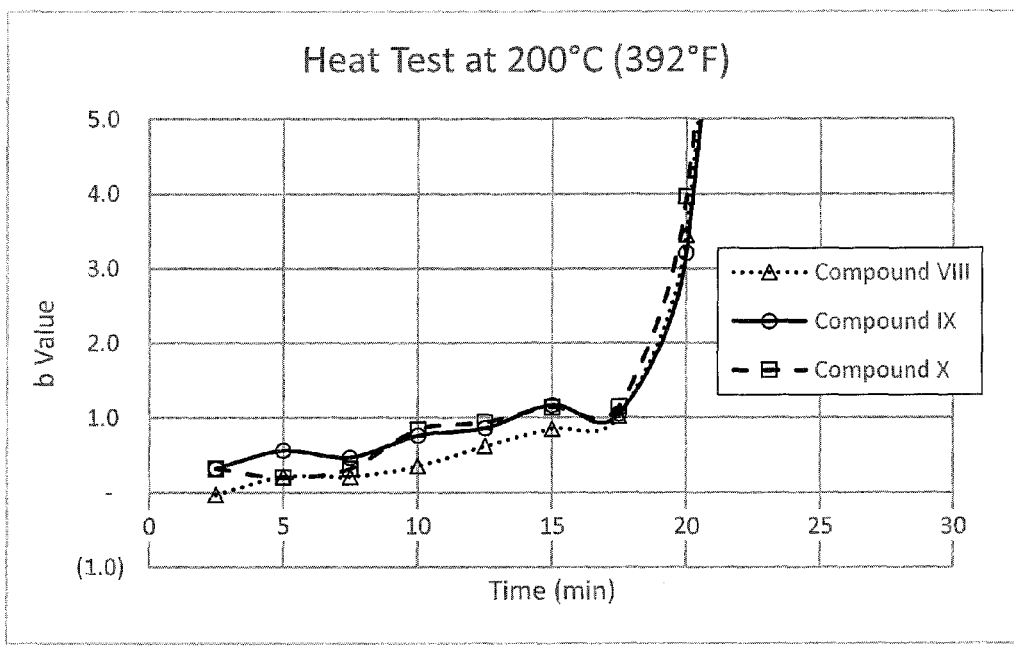

PHENOL-FREE OVERBASED ALKALINE EARTH METAL CARBOXYLATE

BACKGROUND OF THE INVENTION

1. Field of Invention

Synthesis of overbased alkaline earth metal carboxylates lacking phenol, for example, alkylphenols and derivatives thereof, including nonylphenol, is facilitated by use of cyclic ether alcohols in such synthesis.

2. Description of Related Art

In stabilizing thermoplastics such as PVC, conventional acid scavengers such as overbased fatty acid salts can be used. Phenols, such as alkylphenols, especially nonylphenol, are used to synthesize alkylphenates, which are similarly used as stabilizers in thermoplastics. Alkylphenols are interpreted in some living systems as hormones, which can disrupt biological systems. Accordingly, a suitable replacement for alkylphenols and alkylphenates has been sought for use in stabilizing plastics.

SUMMARY

In searching for substitutes for phenols such as alkylphenols, especially nonylphenol, the inventors herein have found that cyclic ether alcohols promote formation of overbased alkaline earth suspensions. Reaction products resulting from the use of such promoters, overbased alkaline earth metal carboxylates are useful as secondary stabilizers and acid scavengers for thermoplastics such as polyvinyl chloride (PVC) and chlorinated polyvinyl chloride. Overbased alkaline earth metal carboxylates made with cyclic ether alcohols instead of alkylphenols eliminate the occurrence of excess alkylphenols in the products. It is believed that cyclic ether alcohols displace waters of hydration on the barium hydroxide. Alkoxide salts may also be formed, such as alkaline earth metal tetrahydrofurfuryl oxide.

Overbased alkaline earth salts are typically small particle suspensions of alkaline earth carbonates in oil carriers. Traditionally, alkylphenols have been used to promote carbonation of alkaline earth hydroxides, and the derived alkylphenate salts have been used as surfactants for the alkaline earth carbonate particulate. Barium alkylphenate is an intermediate in a reaction scheme starting with the reaction of alkylphenols (including nonylphenol) with barium hydroxide (including hydrated forms) which form barium alkylphenates. Hydrated alkylphenates are reacted with carbon dioxide to give barium carbonate and free alkylphenol. The alkylphenol enters back into the reaction cycle. The intermediate 10.7 $pK_a$ value for alkylphenols between carbonic acid ($pK_{a1}$ 3.6 to 6.367 and $pK_{a2}$ 10.329) and water ($pK_{a1}$ 15.7), and the lipophilic nature of the alkylphenol is believed to make such a scheme feasible. Barium is drawn into the organic carrier, typically mineral oil, by means of the reaction sequence in FIG. 1.

It has been discovered that when nonylphenol was replaced with a cyclic ether hydroxide, such as tetrahydrofurfuryl alcohol (THFA), carbonation of alkaline earth hydroxides is similarly promoted. THFA has an intermediate $pK_a$ value, calculated to be 14.44, which supports the possibility of such a scheme. Barium tetrahydrofurfuryl oxide is a likely intermediate as shown in the reaction scheme of FIG. 2. Synthesis of barium tetrahydrofurfuryl oxide from barium hydroxide and tetrahydrofurfuryl alcohol is taught by Halasa, et al. U.S. Pat. No. 7,291,687, which is incorporated herein by reference in its entirety. Barium tetrahydrofurfuryl oxide has the advantage of being soluble in nonpolar solvents.

Cyclic ether alcohols typically have relatively high boiling points. For example THFA has a boiling point of 343-354° F. The relatively high boiling points of cyclic ether alcohols are an advantage in high temperature reactions in comparison with lower molecular weight alcohols, e.g. methanol (bp 148.5° F., $pK_a$ 15.5). THFA forms a roughly 50/50 azeotrope with water thus serving as a vehicle for water removal. The inventors have discovered that a temperature range of 240 to 300° F., or 250-280° F., or in some cases 265-275° F., is suitable for conducting the reactions converting alkaline earth metal hydroxides or other alkaline-earth metal salts to alkaline earth metal carboxylates preparatory to reaction with the cyclic ether alcohol, fatty acid and carbon dioxide, which produces the overbased alkaline earth metal carboxylate of the invention.

Fluorotelomer alcohols have intermediate $pK_a$ values, e.g. 2,2,2-trifluoroethanol (bp 172.4° F., $pK_a$ 12.5) and 1,1,1,3,3,3-hexafluoro-2-propanol (bp 136.5° F., $pK_a$ 9.3). Hence fluorotelomer alcohols might be useful in promoting carbonation of alkaline earth metal solutions. However, like alkylphenols, there are environmental and health concerns about fluorotelomer alcohols that would prohibit the use in final products.

Ethylene glycol methyl ether (bp 255-257° F., $pK_a$ 14.8) has an intermediate $pK_a$ value and a relatively high boiling point. However, there are concerns about the toxicity of ethylene glycols. Ethylene glycol methyl ether is also known as 2-methoxyethanol. 2-Methoxyethanol is included in the Candidate List of Substances of Very High Concern (SVHC) according to Regulation (EC) No. 1907/2006 (REACH). It is advantageous to work with agents of lower health concern than presented by ethylene glycol methyl ether.

Accordingly, an embodiment of the invention is a method of making a phenol-free overbased alkaline earth metal carboxylate comprising: (a) providing and reacting the following to form a reaction mixture: (i) cyclic ether alcohol, (ii) alkaline earth metal hydroxide, and (iii) optionally a hydrocarbon solvent or oil, (b) heating the reaction mixture to a temperature of 250-280° F. distilling water in the process, (c) adding (iv) fatty acid to the reaction mixture, (d) adding (v) carbon dioxide to the reaction mixture, and (e) distilling at a temperature of over 280 to 300° F. to remove residual water, wherein no phenol or compound containing a phenol group is present in the reaction mixture. Some of the cyclic ether alcohol may distill with the water during the process.

Another embodiment of the invention is a plastic or thermoplastic composition including any phenol overbased alkaline earth metal carboxylate made by any method disclosed herein.

An embodiment of the invention is a method of producing a stabilizer package comprising combining: (a) the phenol-free overbased alkaline earth metal carboxylate made by the method disclosed herein, (b) optionally at least one heat stabilizer, and (c) optionally a fatty acid zinc salt. In a preferred embodiment, the at least one heat stabilizer is present. In a preferred embodiment the at least one heat stabilizer is a phosphite stabilizer as elsewhere disclosed herein.

An embodiment of the invention is a method of producing a stabilizer package comprising combining: (a) any phenol-free overbased alkaline earth metal carboxylate disclosed herein or made by any method disclosed herein, (b) optionally at least one heat stabilizer, and (c) optionally a fatty acid zinc salt. Additional stabilizer components that may optionally be included are: phosphites, beta-diketones, polyols, primary antioxidants, plasticizers, lubricants, and other agents known to those skilled in the art. The fatty acid zinc salt may have 4-28 carbons or 5-26 carbons or 6-20 carbons.

An embodiment of the invention is a method of stabilizing a plastic composition comprising: (a) providing a stabilizer package including, (i) a zinc carboxylate primary stabilizer, and (ii) a secondary stabilizer comprising an alkylphenol-free overbased alkaline earth metal carboxylate, (b) providing a plastic composition, and (c) combining the plastic composition with the stabilizer package. The alkylphenol-free overbased alkaline earth metal carboxylate may be any disclosed herein or made by any process disclosed herein.

An embodiment of the invention is a method of stabilizing a plastic composition comprising: (a) providing a stabilizer package including, (i) a zinc carboxylate primary stabilizer, and (ii) any secondary stabilizer made by any method disclosed herein, (b) providing a plastic composition, and (c) combining the plastic composition with the stabilizer package.

The foregoing and other features of the invention are hereinafter more fully described and particularly pointed out in the claims, the following description setting forth in detail certain illustrative embodiments of the invention, these being indicative, however, of but a few of the various ways in which the principles of the invention may be employed.

BRIEF DESCRIPTION OF THE DRAWINGS

FIG. 1. Reaction Scheme including Alkylphenol for producing Overbased Barium Carboxylate.

FIG. 2. Inventive reaction scheme with cyclic ether hydroxide intermediate to make Overbased Barium Carboxylate.

FIG. 3. Graphical representation of Heat Stability Test of Compounds I-IV at 190° C.

FIG. 4. Graphical representation of Heat Stability Test of Compounds V-VII at 190° C.

FIG. 5. Graphical representation of Heat Stability Test of Compounds VIII-X at 190° C.

FIG. 6. Graphical representation of Heat Stability Test of Compounds I-IV at 200° C.

FIG. 7. Graphical representation of Heat Stability Test of Compounds V-VII at 200° C.

FIG. 8. Graphical representation of Heat Stability Test of Compounds VIII-X at 200° C.

DETAILED DESCRIPTION OF THE INVENTION

The compounds of the invention are used to stabilize thermoplastic resins against heat, provide acid scavenging and are considered secondary stabilizers. Metal compound heat stabilizers of halogenated thermoplastic resins, such as vinyl halide resin compositions, are taught herein. These metal compounds serve to capture HCl liberated during heat processing of the halogenated thermoplastic resin composition into its final shape. Hydrogen chloride is also liberated during the service life of the thermoplastic, and the service life of the thermoplastic is often determined by the supply of primary and secondary stabilizers provided with the thermoplastic composition, and the ongoing ability of the stabilizers to effectively remove HCl. The metals forming the focus of the invention are alkaline earth metals: magnesium, calcium, strontium, and barium. Hence in any embodiment disclosed and claimed herein, the alkaline earth metals are envisioned to be any of magnesium, calcium, strontium, and/or barium. Barium and calcium are preferred and barium is most preferred.

The stabilizers are usually metal salts of a carboxylic acid, advantageously of a $C_8$-$C_{24}$ monocarboxylic acid (i.e., fatty acid) such as lauric, oleic, stearic, octoic, or similar fatty acid salts. Other fatty acid chain lengths and branching can be used, for example fatty acids having 4-22 carbons, or 6-20 carbons or 8-18 carbons. Mixed metallic carboxylates involving calcium/zinc or barium/zinc blends alone and in combination with other stabilizers or additives such as phosphites are envisioned. Useful phosphite stabilizers include trilauryl phosphite, trisisodecyl phosphite, diphenyl phosphite, diphenyl isodecyl phosphite, and tetraphenyl dipropylene glycol diphosphite. Others are known to the skilled artisan.

The overbased alkaline earth metal carboxylate of the invention is useful as a secondary stabilizer, or costabilizer for halogenated polymers, for example, poly(vinyl chloride), chlorinated poly(vinyl chloride), fluorochloropolymers, halogenated polyolefins, or in general, copolymers including at least one halogenated monomer.

The invention envisions alkaline earth metal carboxylates. An overbased alkaline earth metal carboxylate is barium carbonate surrounded by an inverted micelle of barium tallate or other barium-fatty acid salts.

Overbased barium carboxylates made with cyclic ether alcohols instead of alkylphenols eliminates the occurrence of excess alkylphenols in the product. The products and processes of the invention are distinguished from those processes using or products made using methanol, polyols or methylcarbitol as well.

Accordingly, an embodiment of the invention is a stabilizer composition including a primary stabilizer (such as zinc 2-ethylhexanoate) and any overbased alkaline earth metal salt (a carboxylate such as barium tallate) disclosed herein or made by any method disclosed herein.

The phenol-free overbased alkaline earth metal carboxylate as made by any process herein or as disclosed herein may be contained in a thermoplastic composition, or halogenated polymer.

The invention envisions production of phenol-free overbased alkaline earth metal salts of fatty acids involving a reaction of the following components.

Alkaline earth metal salts. The secondary stabilizer of the invention has at its core, an alkaline earth metal. Such group II elements are introduced in the form of a salt such as barium hydroxide, calcium hydroxide, or magnesium hydroxide. The oxides and hydrates of alkaline earth elements and combinations thereof are also envisioned.

Throughout this specification and claims, the term "basic" or "overbased" as applied to the alkaline earth metal salts is used to refer to metal compositions wherein the ratio of total metal contained therein to the fatty acid moieties is greater than the stoichiometric ratio of the neutral metal salt. That is, the number of metal equivalents is greater than the number of equivalents of the fatty acid. In some instances, the degree to which excess metal is found in the basic metal salt is described in terms of a "metal ratio." The phrase "metal ratio" as used herein indicates the ratio of total alkaline earth metal in the oil-soluble composition to the number of equivalents of the fatty acid or organic moiety. The basic metal salts often have been referred to in the art as "overbased" or "superbased" to indicate the presence of an excess of the basic component.

Cyclic Ether Alcohol. In place of alkylphenols that are used to make traditional secondary stabilizers, cyclic ether alcohols are used. Cyclic ether alcohols displace water from the reaction, and lead to intermediate barium alkoxides. The cyclic ether alcohols envisioned to be useful herein have $pK_a$ values of 12 to 15, preferably 12.5 to 14.5 and more preferably 13 to 14, and are not categorized as SVHC. No residual alkylphenol is possible in such a reaction scheme. Furanose and pyranose cyclic structures with appended alcohols comprise a subset of these cyclic ether alcohols.

Suitable cyclic ether alcohols include but are not limited to sorbitan, sorbitan monolaurate, sorbitan monooleate, coconut fatty acid monoesters with sorbitan, sorbitan sesquioleate, sorbitan trioleate, 1,4-anhydroglucitol (1,4-sorbitan; $pK_a$ 13.69 [determined according to Ref. 1: Advanced Chemistry Development (ACD/Labs) Software V11.02 © 1994-2014 ACD/Labs)]), 1,5-anhydroglucitol (1-deoxyglucose or 1,5-sorbitan; $pK_a$ 13.44 [Ref. 1]), 2,5-anhydroglucitol (2,5-sorbitan; $pK_a$ 13.26 [Ref 1]) 1,4-anhydroallitol, 1,5-anhydroallitol, 1,5-anhydromanitol, deoxyribose, isosorbide (dianhydroglucitol, $pK_a$ 13.17 [Ref 1]), isomannide (dianhydromannitol), 2-deoxyglucose (p$K_a$ 12.52 [Lange's Handbook, Table 8.8]), tetrahydrofurfuryl alcohol (p$K_a$ 14.44 [Ref 1]), tetrahydropyran-2-methanol (p$K_a$ 14.48 [Ref 1]), 2,5-bis(hydroxymethyl)tetrahydrofuran (p$K_a$ 14.14 [Ref 1]), 2,2-bis(hydroxymethyl)tetrahydrofuran, 2-(hydroxymethyl)-3-hydroxytetrahydrofuran, 2,2-bis(hydroxymethyl)tetrahydropyran (p$K_a$ 14.18 [Ref. 1]) and 1,8,14-trioxatrispiro [4,1,4,1,4,1] octadecane-6, 12, 18-triol, each alone or in any combination.

Preferred cyclic ether alcohols include tetrahydrofurfuryl alcohol, tetrhydropyran-2-methanol, 2,5-bis(hydroxymethyl)tetrahydrofuran, 2,2-bis(hydroxymethyl)tetrahydrofuran, and 2,2-bis(hydroxymethyl)tetrahydropyran. Most preferred is tetrahydrofurfuryl alcohol.

Carbonation. To form the carboxylates of the invention, carbon dioxide must be bubbled through a reaction mixture including an alkaline earth metal salt (such as calcium hydroxide or barium hydroxide, including the hydrated forms thereof), a cyclic ether alcohol, fatty acid and optional fatty alcohol. Carbon dioxide may be bubbled through the reaction mixture at a rate of 100, 200, 250, 300, 400, 500, or 1000 ml per minute or values in between for a time of 30, 50, 60, 75, 90, 100, or 120 minutes or values in between. The rate and duration of carbon dioxide addition being determined by the efficiency of the reaction and equipment. Sparge rings with a number of small holes are generally more efficient in dispersing gases in fluids than is a straight subsurface tube. Likewise hollow impellers, with an inlet hole on the hollow shaft above the liquid level and outlets on the impeller blades below the surface, can be used to better entrain gases. Baffling can introduce turbulence helping to prolong gas residence in the liquid. The effect of efficient agitation in dispersing unreacted barium hydroxide and in entraining carbon dioxide is of great importance.

Fatty Acid. The fatty acid can be any fatty acid having 4-28 carbon atoms, preferably 6-22 carbon atoms, including butyric, pentanoic, hexanoic, heptanoic, capyrilic, capric, pelargonic, lauric, myristic, myristoleic, palmitic, palmitoleic, sapienic, stearic, oleic, elaidic, vaccenic, linoleic, linoelaidic, α-linolenic, arachidic, arachidonic, eicosapentenoic, erucic, docosahexaenoic, behenic, lignoceric, cerotic, and combinations thereof. Branched carboxylic acids such as neodecanoic acid, naphthenic acid can also be used to good effect. Preferred are acids derived from natural sources with naturally occurring acid distributions. Most preferred are tall oil fatty acids and soybean oil fatty acids.

Fatty Alcohol. The method of the invention may include in the reaction mixture a fatty alcohol having the formula $CH_3(CR^1R^2)_n$—OH, where n is 4 to 22, and $R^1$ and $R^2$ are independently $C_1$-$C_3$ alkyl groups. Such fatty alcohols have a p$K_a$ value typically between 15 and 18. Suitable fatty alcohols may be selected from among octanol (p$K_a$ 15.27 [Ref 1]), 2-ethylhexanol (p$K_a$ 15.05 [Ref 1]), nonanol (p$K_a$ 15.22 [Ref 1]), isononanol, decanol (p$K_a$ 15.21 [Ref 1]), isodecanol, 2-propylheptanol (p$K_a$ 15.09 [Ref 1]), undecyl alcohol (p$K_a$ 15.20 [Ref 1]), lauryl alcohol (p$K_a$ 16.00 [Veith, U.S. EPA QSAR system, ERL-Duluth, 1985.], 15.20 [Ref 1]), isotridecanol, and coconut fatty alcohol.

Liquid Hydrocarbon Carrier. The liquid hydrocarbon is a carrier for the largely hydrophobic constituents of the reaction of the invention. Alkanes, in particular, petroleum distillates, having about 15 to about 40 carbons are envisioned as the carrier. Paraffinic oils (linear alkanes) and naphthenic oils (cycloalkanes) are useful, but not aromatic oils, as the presence of aromatic compounds is inimical to environmental concerns in various countries.

Heat stabilizers that include alkylphenol-free overbased barium carboxylates derived using cyclic ether alcohols are useful for PVC compounds. The inclusion of the cyclic ether alcohols should not impair the efficacy of the heat stabilizers. Beneficially the invention herein will not contribute to the nonylphenol content of such stabilizers.

The process of the present invention may be used to prepare liquids of the alkaline earth metal carboxylates of the fatty acids. The method may be practiced without the use of a phenol promoter or phenolic reaction product. Therefore, liquid overbased barium fatty acid carboxylates have been made without the need for a phenol or phenolic reaction product in order to achieve a haze-free liquid. In the case of liquid overbased calcium fatty acid carboxylates, haze-free products are obtained without a phenol where the cyclic ether alcohol having at least 5 carbon atoms is employed.

A halogen-containing polymer, such as a vinyl halide resin, most commonly stabilized with the basic metal salts of this invention is polyvinyl chloride. It is to be understood, however, that this invention is not limited to a particular vinyl halide resin such as polyvinyl chloride or its copolymers. Other halogen-containing resins which are employed and which illustrate the principles of this invention include chlorinated polyethylene, chlorosulfonated polyethylene, chlorinated polyvinyl chloride, and other vinyl halide resin types. Vinyl halide resin, as understood herein, and as appreciated in the art, is a broad term and is adopted to define those resins or polymers usually derived by polymerization or copolymerization of vinyl monomers including vinyl chloride with or without other comonomers such as ethylene, propylene, vinyl acetate, vinyl ethers, vinylidene chloride, methacrylate, acrylates, styrene, etc. A simple case is the conversion of vinyl chloride $H_2C$=CHCl to polyvinyl chloride ($CH_2CHCl$—) wherein the halogen is bonded to the carbon atoms of the carbon chain of the polymer. Other examples of such vinyl halide resins would include vinylidene chloride polymers, vinyl chloride-vinyl ester copolymers, vinyl chloride-vinyl ether copolymers, vinyl chloride-vinylidene copolymers, vinyl chloride-propylene copolymers, chlorinated polyethylene, and the like. Of course, the vinyl halide commonly used in the industry is the chloride, although others such as bromide and fluoride may be used. Examples of the latter polymers include polyvinyl bromide, polyvinyl fluoride, and copolymers thereof. Copolymers and combinations of any of the foregoing are also suitable.

An embodiment of the invention is a plastic mass or plastic article including any stabilizer or any phenol-free overbased alkaline earth metal carboxylate made by any method disclosed herein.

EXAMPLES

Comparative Example

Using a linear fatty alcohol, an attempt at making an overbased barium carboxylate resulted in unreacted barium hydroxide remaining after the reaction mixture was exposed to carbon dioxide. In this attempt, 26.85 g linear alkyl benzene, 204.00 g mineral oil, 56.02 g C 10-18 fatty alcohol, 175.50 g of barium hydroxide monohydrate, and 1.01 g zinc oxide were combined and heated to 156° C. before adding 130.01 g oleic acid over the course of 50 minutes. Thereafter carbon dioxide was added at the rate of 500 standard ml per minute for 40 minutes while maintaining 154° C. During the course of the reaction only 10 ml of aqueous distillate was collected. When the liquid was decanted from the reaction vessel, 132.38 g of wet crystalline solids was discovered. These crystalline solids were soluble and alkaline in water, which is consistent with starting barium hydroxide hydrate.

Inventive Example 1

In this reaction, 26.62 g linear alkyl benzene, 56.02 g tetrahydrofurfuryl alcohol, 204.03 g mineral oil, 0.04 g Viscoplex® 14-515 antifoam (produced by Evonik), and 175.50 g barium hydroxide monohydrate crystals were combined and heated to 151° C. Thereupon 130.08 g oleic acid was added over the course of 2 hours. Carbon dioxide was then added at 500 standard ml per minute for 37 minutes. Vacuum was applied for 10 minutes. During the reaction 42.68 g aqueous distillate was collected. 15.03 g Hyflo® Supercel® filter aid (produced by Imerys Filtration Minerals) was added to the reaction product, which was filtered through 10 micron cellulose filter media. The final product was an amber oil containing 21.8% Ba in agreement with theory. A base number of 36.9 mg KOH/g was recorded for the sample. This example demonstrates that the fatty alcohol is not necessary to effect carbonation of the barium hydroxide.

Inventive Example 2

Mineral oil replaced with a white mineral oil and the linear alkyl benzene was replaced with isotridecanol. The isotridecanol allows the cyclic ether alcohol with the mineral oil to coalesce giving a clear, homogeneous mixture prior to addition of the barium hydroxide hydrate and likely in the final product. In this reaction, 51.07 g tetrahydrofurfuryl alcohol, 208.13 g white mineral oil, 50.09 g isotridecanol, 0.10 g Viscoplex® 14-515 antifoam, and 189.37 g barium hydroxide monohydrate crystals were combined and heated to 153° C. Thereupon 140.28 g oleic acid was added over the course of 65 minutes. Carbon dioxide was then added at 500 standard ml per minute for 45 minutes. During the reaction 46.07 g aqueous distillate was collected. An additional 6.63 g of aqueous distillate was removed under vacuum over 22 minutes. 14.00 g Hyflo® Supercel® filter aid, available from Sigma-Aldrich, St. Louis, Mo., was added to the reaction product, which was filtered through 10 micron cellulose filter media. The result was a clear yellow oil containing 19.8% Ba. A base number of 3.6 mg KOH/g was recorded for the sample.

Inventive Example 3

The oleic acid was replaced with tall oil fatty acids. In this reaction, 220.0 g hydrotreated light petroleum distillates, 40.00 g tetrahydrofurfuryl alcohol, 40.00 g isotridecanol, 0.50 g poly(dimethyl siloxane), and 189.37 g barium hydroxide monohydrate crystals were combined and heated to 150° C. Thereupon 142.42 g tall oil fatty acid was added over the course of 98 minutes. Carbon dioxide was then added at 150 standard ml per minute for 2.5 hours. During the reaction 37.85 g aqueous distillate was collected. An additional 5.61 g of aqueous distillate was removed under vacuum down to 204 mm Hg pressure over 32 minutes. The crude product was filtered with ~20 psig applied inert gas pressure sequentially through: a nominal 25 μm porosity polyethylene fabric, 10 micron cellulose filter media, 5 micron cellulose filter media, and 1 micron cellulose filter media. To obtain a clear product, Whatman® 4 paper (produced by GE Healthcare Life Sciences) was precoated with a slurry consisting of 101.4 g of material from the previous filtration and 14.00 g Hyflo® Supercel® filter aid. The product was filtered through the precoated filter with applied ~22 psig inert gas pressure resulting in a clear yellow oil containing 21.1% Ba. A base number of 20 mg KOH/g was recorded for the sample.

In the examples above, aqueous distillate was found to contain roughly 10% tetrahydrofuruyl alcohol by analysis of IR spectra. More tetrahydrofurfuryl alcohol (20-50%) was found in distillate, and the aqueous distillate was turbid when vacuum was applied. Further distillation or steam distillation might remove most of the cyclic ether alcohol from the overbased barium carboxylate.

The base number (mg KOH/g product) of the final products are a measure of the filterability of the product. As the reaction proceeds, the base number of the reaction mixture decreases. A base number in the range of 3-40 indicates satisfactory filterability. More preferred is a base number in the range of 10-15. However, lower base numbers can also lead to satisfactory filterability. Excess barium hydroxide and barium carbonate should be filtered out. Particles over 2 microns should be filtered out to make a clear stabilizer composition.

Heat Test Procedure: The PVC resin, stearic acid, plasticizer, epoxidized soybean oil, and stabilizer are mixed with a spatula by hand and then milled for 5 minutes at 320° F. on a two-roll mill. The cooled sheet is cut into strips. Those strips are placed in a Mathis Oven at 200° C. and conveyed out of the oven at a rate of 4 mm/min Comparison of the yellowing and burn point was made between samples. Table 1 were made using the inventive nonylphenol-free overbased barium tallate (22% Ba) of Example 1 or Example 3. Comparative Stabilizers A, D, E, and H were formulated with conventional overbased barium intermediate that contains barium nonylphenate and barium carboxylate (35.5% Ba Intermediate). Due to the difference in Ba content, the 35.5% Ba Intermediate was diluted either with phenyl diisodecyl phosphite or with a hydrocarbon solvent to provide equivalent Ba content to the stabilizer.

TABLE 1

Stabilizer Formulations

| Components (wt %) | A | B | C | D | E | F | G | H | J | K |
|---|---|---|---|---|---|---|---|---|---|---|
| Phenyl Diisodecyl Phosphite | 68.72 | 62.63 | 68.63 | 68.63 | — | — | — | — | — | — |
| Trilauryl Phosphite | — | — | — | — | 62.63 | 62.63 | 62.63 | 68.63 | 68.63 | 68.63 |
| Oleic Acid | 4.00 | 4.00 | — | — | 4.00 | 4.00 | 4.00 | — | — | — |
| Hydrocarbon Solvent | — | — | — | 6.09 | 6.09 | — | — | 6.09 | — | — |
| Amyl Acid Phosphate | 2.00 | 2.00 | — | — | 2.00 | 2.00 | 2.00 | — | — | — |
| 16% Zinc 2-Ethylhexanoate | 15.70 | 15.70 | 15.70 | 15.70 | 15.70 | 15.70 | 15.70 | 15.70 | 15.70 | 15.70 |
| 35.5 % Ba Intermediate | 9.58 | — | — | 9.58 | 9.58 | — | — | 9.58 | — | — |
| Product of Example 1 | — | — | — | — | — | 15.67 | — | — | 15.67 | — |
| Product of Example 3 | — | 15.67 | 15.67 | — | — | — | 15.67 | — | — | 15.67 |
| Dibenzoylmethane | — | — | — | — | — | — | — | 2.00 | 2.00 | 2.00 |

A PVC homopolymer suspension resin, OxyVinyls® 226F (commercially available from Oxy Vinyls LP, Dallas, Tex.) was blended with components in the ratio found in Table 2 and Table 3. Selected stabilizers are as found in Table 4 and Table 5. The mix was then milled using a two-roll mill to 30-35 mils thickness for 5 minutes with the rolls maintained at 160° C. (320° F.). Sheets were cut into 20 mm wide strips. Heat tests were carried out on the strips using a Mathis Oven at 190° C. (374° F.) or 200° C. (392° F.) with a tray speed of 8 mm/min. Colorimeter Hunter Lab readings were taken at 20 mm intervals along the strips. Greater b-values indicate greater yellowness, which is undesirable. When considering color preservation of final articles, minimal changes in b-values from beginning to end of test are desirable. As recorded in Table 4 and Table 5, resulting b-values (yellow-blue contribution) for Compounds II, III, VII, and X demonstrate the effectiveness of the inventive nonylphenol-free overbased barium intermediate of Example 3 relative to Comparative Compounds I, IV, V, and VIII, respectively. Compounds VI and IX demonstrate the effectiveness of the inventive nonylphenol-free overbased barium intermediate of Example 1 relative to Comparative Compounds V and VIII, respectively.

TABLE 2

PVC Compound Formulations I-IV

| | phr* |
|---|---|
| Oxy Vinyls ® 226F PVC | 100.00 |
| Stearic Acid | 0.25 |
| Diisononyl Phthalate | 40.00 |
| Plas-Chek ® 775 ESO | 5.00 |
| Selected Stabilizer | 2.00 |
| | 147.25 |

TABLE 3

PVC Compound Formulations V-X

| | phr* |
|---|---|
| Oxy Vinyls ® 226F PVC | 100.00 |
| Stearic Acid | 0.25 |
| Diisodecyl Phthalate | 40.00 |
| Plas-Chek ® 775 ESO | 5.00 |
| Selected Stabilizer | 2.00 |
| | 147.25 |

*phr is parts per hundred resin. Plas-Chek® 775 ESO is epoxidized soybean oil produced by Ferro Corporation.

TABLE 4

Hunter b-Values for Test at 190° C. (374° F.)

| Compound | Stabilizer | 2.5 | 5.0 | 7.5 | 10.0 | 12.5 | 15.0 | 17.5 | 20.0 | 22.5 | 25.0 | 27.5 | 30.0 | Change |
|---|---|---|---|---|---|---|---|---|---|---|---|---|---|---|
| I | A | 0.13 | 0.25 | 0.19 | 1.09 | 1.78 | 2.86 | 3.00 | 2.93 | 2.65 | 2.74 | 2.89 | 4.25 | 4.12 |
| II | B | 0.98 | 1.20 | 1.29 | 2.04 | 2.55 | 2.97 | 2.94 | 2.90 | 2.75 | 2.55 | 2.63 | 3.10 | 2.12 |
| III | C | 0.33 | 0.59 | 0.80 | 1.85 | 3.83 | 4.47 | 4.51 | 4.53 | 3.91 | 3.70 | 3.31 | 3.91 | 3.58 |
| IV | D | 0.09 | −0.07 | 0.07 | 0.52 | 1.91 | 3.36 | 3.89 | 3.78 | 3.73 | 3.38 | 3.05 | 4.23 | 4.14 |
| V | E | −0.13 | −0.13 | 0.00 | 0.42 | 1.31 | 2.31 | 2.80 | 2.71 | 2.53 | 2.61 | 3.07 | 7.45 | 7.58 |
| VI | F | 0.19 | 0.04 | 0.15 | 0.77 | 0.94 | 1.68 | 1.73 | 2.12 | 2.50 | 2.63 | 3.97 | 9.21 | 9.02 |
| VII | G | 0.30 | 0.18 | 0.21 | 0.58 | 1.06 | 1.88 | 1.95 | 2.25 | 2.24 | 2.47 | 4.47 | 10.14 | 9.84 |
| VIII | H | −0.21 | −0.23 | −0.07 | 0.16 | 0.30 | 0.58 | 0.50 | 0.58 | 0.57 | 1.23 | 3.24 | 8.01 | 8.22 |
| IX | J | −0.24 | −0.10 | −0.17 | 0.22 | 0.57 | 0.63 | 0.88 | 0.91 | 1.07 | 1.52 | 3.36 | 9.43 | 9.67 |
| X | K | −0.19 | −0.09 | −0.07 | 0.16 | 0.41 | 0.63 | 0.79 | 0.94 | 0.95 | 1.41 | 3.40 | 8.89 | 9.08 |

TABLE 5

Hunter b-Values for Test at 200° C. (392° F.)

| Compound | Stabilizer | 2.5 | 5.0 | 7.5 | 10.0 | 12.5 | 15.0 | 17.5 | 20.0 | Change |
|---|---|---|---|---|---|---|---|---|---|---|
| I | A | 0.35 | 0.42 | 1.05 | 1.71 | 3.17 | 3.11 | 2.69 | 3.73 | 3.38 |
| II | B | 0.93 | 0.93 | 1.37 | 2.29 | 2.77 | 2.80 | 2.47 | 3.07 | 2.14 |
| III | C | 0.32 | 0.64 | 0.99 | 3.45 | 4.77 | 4.22 | 3.81 | 3.61 | 3.29 |
| IV | D | 0.06 | −0.05 | 0.25 | 1.81 | 3.57 | 3.78 | 3.42 | 3.87 | 3.81 |
| V | E | −0.07 | 0.10 | 0.25 | 0.75 | 2.29 | 3.05 | 2.60 | 3.08 | 3.15 |
| VI | F | 0.65 | 0.71 | 0.84 | 1.38 | 2.09 | 2.39 | 1.83 | 2.61 | 1.96 |
| VII | G | 0.52 | 0.57 | 0.64 | 1.57 | 2.13 | 1.94 | 2.28 | 3.95 | 3.43 |
| VIII | H | −0.03 | 0.21 | 0.21 | 0.35 | 0.62 | 0.85 | 1.02 | 3.45 | 3.48 |
| IX | J | 0.32 | 0.56 | 0.47 | 0.76 | 0.86 | 1.17 | 1.05 | 3.21 | 2.89 |
| X | K | 0.32 | 0.20 | 0.32 | 0.84 | 0.94 | 1.14 | 1.15 | 3.96 | 3.64 |

Many other benefits will no doubt become apparent from future application and development of this technology. All patents, published applications, and articles noted herein are hereby incorporated by reference in their entirety.

As described hereinabove, the present invention solves many problems associated with conventional stabilizers. However, it will be appreciated that various changes in the details, materials and formulations, which have been herein described and illustrated in order to explain the nature of the invention, may be made by those skilled in the art without departing from the principle and scope of the invention, as expressed in the appended claims.

The invention claimed is:

1. A plastic composition including the phenol-free overbased alkaline earth metal carboxylate made by a method comprising:
   a. providing and reacting the following to form a reaction mixture:
      i. cyclic ether alcohol,
      ii. alkaline earth metal hydroxide, and
      iii. optionally a hydrocarbon solvent or oil and
   b. heating the reaction mixture to a temperature of 250-280° F.,
   c. adding (iv) a fatty acid to the reaction mixture,
   d. adding (v) carbon dioxide to the reaction mixture, to produce the phenol-free overbased alkaline earth metal carboxylate and water, and
   e. distilling at a temperature of over 280 to 300° F. to remove residual water, wherein no phenol or compound containing a phenol group is present in the reaction mixture.

2. A halogenated polymer including the phenol-free overbased alkaline earth metal carboxylate made by a method comprising:
   a. providing and reacting the following to form a reaction mixture:
      i. cyclic ether alcohol,
      ii. alkaline earth metal hydroxide, and
      iii. optionally a hydrocarbon solvent or oil and
   b. heating the reaction mixture to a temperature of 250-280° F.,
   c. adding (iv) a fatty acid to the reaction mixture,
   d. adding (v) carbon dioxide to the reaction mixture, to produce the phenol-free overbased alkaline earth metal carboxylate and water, and
   e. distilling at a temperature of over 280 to 300° F. to remove residual water, wherein no phenol or compound containing a phenol group is present in the reaction mixture.

3. The halogenated polymer of claim 2, wherein the halogenated polymer is selected from the group consisting of vinyl halide resin, polyvinyl chloride, copolymers of polyvinyl chloride, chlorinated polyethylene, chlorosulfonated polyethylene, chlorinated polyvinyl chloride, vinylidene chloride polymers, vinyl chloride-vinyl ester copolymers, vinyl chloride-vinyl ether copolymers, vinyl chloride-vinylidene copolymers, vinyl chloride-propylene copolymers, chlorinated polyethylene, polyvinyl bromide, polyvinyl fluoride, copolymers thereof and combinations thereof.

* * * * *